(12) United States Patent
Selner

(10) Patent No.: US 7,601,371 B2
(45) Date of Patent: Oct. 13, 2009

(54) PENETRATING CARRIER, ANTI-FUNGAL COMPOSITION USING THE SAME AND METHOD FOR TREATMENT OF DERMATOPHYTES

(76) Inventor: Marc Selner, 4335 Laurel Canyon Blvd., Studio City, CA (US) 91604

( * ) Notice: Subject to any disclaimer, the term of this patent is extended or adjusted under 35 U.S.C. 154(b) by 0 days.

(21) Appl. No.: 11/684,869

(22) Filed: Mar. 12, 2007

(65) Prior Publication Data
US 2007/0160551 A1    Jul. 12, 2007

Related U.S. Application Data

(62) Division of application No. 10/956,073, filed on Oct. 4, 2004.

(51) Int. Cl.
| A61K 36/61 | (2006.01) |
| A61K 36/534 | (2006.01) |
| A61K 36/00 | (2006.01) |
| A61K 36/13 | (2006.01) |
| H01B 3/22 | (2006.01) |
| C09F 1/00 | (2006.01) |

(52) U.S. Cl. .................. 424/742; 424/747; 424/770; 424/776; 424/739; 585/6.6; 514/939; 530/204

(58) Field of Classification Search ........................ None
See application file for complete search history.

(56) References Cited

U.S. PATENT DOCUMENTS

| 2,536,983 | A | * | 1/1951 | Owen .................. 424/78.17 |
| 4,919,934 | A | | 4/1990 | Deckner et al. |
| 4,927,631 | A | | 5/1990 | Bates |
| 4,933,175 | A | | 6/1990 | Passarelli |
| 5,000,954 | A | | 3/1991 | Stadtmueller |
| 5,658,584 | A | * | 8/1997 | Yamaguchi .................. 424/405 |
| 6,042,845 | A | | 3/2000 | Sun et al. |
| 6,090,403 | A | | 7/2000 | Block et al. |
| 6,344,190 | B1 | | 2/2002 | Nair et al. |
| 6,361,785 | B1 | | 3/2002 | Nair et al. |
| 6,413,555 | B1 | | 7/2002 | Lee |
| 6,541,042 | B1 | | 4/2003 | Frater-Schroder et al. |
| 6,673,756 | B2 | | 1/2004 | Sonnenberg et al. |
| 2002/0034489 | A1 | * | 3/2002 | Wiegland et al. ......... 424/70.24 |
| 2003/0198611 | A1 | | 10/2003 | Glassman et al. |
| 2004/0071757 | A1 | | 4/2004 | Rolf |
| 2005/0014730 | A1 | | 1/2005 | Carlson et al. |

FOREIGN PATENT DOCUMENTS

| DE | 19635659 A1 | * | 3/1998 |
| EP | 0070525 A2 | * | 1/1983 |
| EP | 0 093 563 A2 | | 11/1983 |
| WO | WO 99/36033 | | 7/1999 |
| WO | WO 0222115 A2 | * | 3/2002 |
| WO | WO 2006/041527 A1 | | 4/2006 |

OTHER PUBLICATIONS

"The People's Pharmacy". Gradeons' Guide to Unique Uses for Vick. 2002, pp. 1-4 (particularly page 1).*
"Herbal FungX" Internet Archive Date: Apr. 28, 2004 [Retrieved on: Dec. 18, 2007]. Retrieved from the Internet: http://web.archive.org/web/*/http://www.herbalremedies.com/toenailfungus.html.*
http://www.dermatologychannel.net/fungalinfections/treatment.shtml Jul. 17, 2005.
http:/www.waybackmachine.org Jul. 17, 2005.
http://web.archive.org/web/20030921075049/http://www.blendwell.co.za/prod_index.htm (Web Publication Date: Sep. 21, 2003). Date Accessed: May 2, 2006.
Xiaoying Hui, et al. "Ciclopirox Delivery into the Human Nail Plate" Journal of Pharmaceutical Sciences, vol. 93, No. 10, Oct. 2004, pp. 2545-2548.
Xiaoying Hui, et al. "Nail penetration: enhancement of topical delivery of antifungal drugs by chemical modification of the human nail" TextBook of Cosmetic Dermatology, Third Edition, 2005, pp. 57-63.
R.S. Ramsewak, et al., "In Vitro Antagonistic Activity of Monoterpenes and Their Mixtures Against Toe Nail Fungus Pathogens", Phytotherapy Research, 17, 2003, pp. 376-379, XP-002527754.
M.S. Ali-Shtayeh, et al. "Antifungal Activity of Plant Extracts Against Dermatophyes", Mycoses, 42, 1999, pp. 655-672, XP-001182623.
EP 05 73 5368 Jun. 24, 2009 European Search Report.
2005800337137 PR China Intellectual Property Office May 22, 2009.

* cited by examiner

*Primary Examiner*—Christopher R Tate
*Assistant Examiner*—Amy L Clark
(74) *Attorney, Agent, or Firm*—Oblon, Spivak, McClelland, Maier & Neustadt. L.L.P.

(57) ABSTRACT

A liquid carrier for topical administration is provided that contains a mineral oil, turpentine and, optionally, camphor, and optionally other terpenoid components containing pinene, and its use to provide an antifungal composition containing a mixture of antifungal essential oils and the carrier system, wherein the mixture of antifungal essential oils includes an effective amount of each of *Eucalyptus globulus*, peppermint, cedarwood, and Manuka; along with the use of this composition in the topical treatment of fungal infection, particularly of the nail.

17 Claims, No Drawings

PENETRATING CARRIER, ANTI-FUNGAL COMPOSITION USING THE SAME AND METHOD FOR TREATMENT OF DERMATOPHYTES

BACKGROUND OF THE INVENTION

1. Field of Invention

The present invention relates to a carrier for a topical medicament having improved ability to penetrate thick keratinous tissues, a topical anti-fungal composition useful for the treatment of dermatophytes infection in the nail bed and nail plate and a method for treating fungal nail infections using the composition.

2. Discussion of the Background

Dermatophytes are filamentous fungi that are commonly found in plants and soil. Nail invasion by these organisms cause disease, with thickening, discoloration, odor, decay, lysis (loosening of the nail plate from the base of the nail bed), and deformity such as increased curvature of the nail plate. In addition to dermatophytes, *candida albecans* (a yeast) is also a common pathogen. A small number of diseases are also caused by molds, considered non-dermatophytes. The medical name for fungal nail disease is onychomycosis. Fungi live in the nail bed under the toenail and also involve the nail itself. The fungus is a parasite, and lives on the keratin, by dissolving the keratin with enzymes known as keratinases. The most common organisms are *Trichophytan Rubrum* (which causes between 80-90% of infections), *Trichophytan Mentagrophytes, Epidermophytan Floccosum* and *Candida Albecans*.

Many times the fungi will cause the nail to produce excess keratin, a condition known as hyperkeratosis, causing the nail to be thicker and often deformed. Additionally, the thicker toenail can cause pain, leading to ingrown nails, and even difficulty in wearing shoes due to the thickness. The typical treatment for this condition involves having a podiatrist debride or manually thin the nail, often at great cost to the patient, insurance, and Medicare.

Nails are made of layers of Keratin a protein, which has lipid bilayers, phospholipid cell membranes and connections between the cells called desmosomes. The cells of the toenails are dead, so penetration relies on diffusion of non polar lipids (non charged) across these structures. The more fat soluble, the better the penetration. To effectively treat onychomycosis, it is necessary to get the antifungal medicine through the nail plate and keratin, which may be very thick, and penetrate to the site where the organism lives.

One U.S. study suggested a prevalence of Onychomycosis of 18.5% with the number of persons affected on the rise, which may be partly accounted for by the aging U.S. population. Onychomycosis affects 32% of the people between 60-70 years of age, and some studies suggest it may affect 48% of the population by age 70. Onychomycosis has a stronger prevalence in immunosuppressed people, such as those with diabetes, poor circulation, or HIV infection. Toenail infections are several times more common than fingernail infections. Several oral medicines are effective in treating these conditions, such as Lamisil and Sporonox. However, these medicines are prescription medications, costing the patient as much as $1000 to treat an infection, and requiring extraneous lab tests, because they can cause damage to the liver and kidneys as well as other side effects.

Topical treatments have historically been somewhat ineffective. One such topical treatment is Penlac, which is at the top of the list, but requires a prescription, monthly treatments by the doctor to debride or remove the dead nail tissue and is expensive (with a small bottle of 6 cc costing typically over $150). Additionally it is only indicated for disease of the nail distal to the lunula-white half moon. According to the Physician's Desk Reference (PDR), two studies using Penlac indicate cure rates of 5.5% and 8.5%, and an almost cure rate of 6.5% and 12%. Further, the PDR states that Penlac is not effective against the most common fungus to infect nails, *Trichophytan Rubrum*. There other OTC medicines but proof of their efficacy is difficult to determine.

SUMMARY OF THE INVENTION

Accordingly, one object of the present invention is to provide a carrier for topical medicaments that can penetrate and transport a broad spectrum of antifungal compounds through keratinous tissues, such as nail bed and nail plate.

A further object of the present invention is to provide a topical composition for treatment of fungal infections using this carrier.

A further object of the present invention is to provide a topical anti-fungal composition effective at treating onychomycosis.

A further object of the present invention is to provide a topical anti-fungal composition that contains only GRAS ingredients, and requires no debridement during treatment.

A further object of the present invention is to provide a method for the topical treatment of nail infections using such anti-fungal compositions.

These and other objects of the present invention have been satisfied by the discovery of a liquid carrier system comprising a mineral oil and turpentine, and optionally, camphor and/or one or more additional terpenoid components containing pinene, and its use to prepare an anti-fungal composition, comprising:

an effective anti-fungal amount of a mixture of antifungal essential oils and the carrier system, wherein the mixture of antifungal essential oils comprises effective amounts of each of *eucalyptus globulus*, peppermint, cedarwood, and manuka.

DETAILED DESCRIPTION OF THE INVENTION

The present invention relates to a liquid carrier system comprising a mineral oil, turpentine, and optionally, camphor and/or one or more additional terpenoid components containing pinene. When combined with one or more active ingredients, this carrier system provides penetration of keratinous tissue and transport and delivery of the active ingredient to the site in need thereof.

The present invention further relates to an anti-fungal composition, comprising:

an effective anti-fungal amount of a mixture of antifungal essential oils and a carrier system, wherein the mixture of antifungal essential oils comprises effective amounts of each of *eucalyptus globulus*, peppermint, cedarwood, and Manuka; and wherein the carrier system is as described above.

The antifungal composition of the present invention is preferably in the form of a liquid, containing slow-to-evaporate whole antifungal oils in a proven carrier. The carrier system is one important aspect of the present invention, as it provides the ability to take the fat soluble substances and penetrate the thick keratin layer of the nail in an effective manner. The combination of antifungal essential oils has been found to be effective on most or all of the different types of fungal infections of the nail (particularly the toenail) in a broad spectrum. Further, the combination preferably helps overcome the resistance of the different fungi as they mutate and change in an attempt to avoid being destroyed. The composition is preferably in a liquid form, since liquids have the best penetration. Further, the composition is most preferably in a liquid carrier that is a non evaporative substance, particularly preferably the carrier system of the present invention. With evaporation, the carrier tends to disappear before it can penetrate the thick nail plate.

In a most preferred embodiment, the carrier of the present invention, when put on a non absorbtive material, does not significantly evaporate over a period of days, and most preferably has essentially a negligible vapor pressure under normal atmospheric conditions, thus exhibiting no observable evaporation to any significant extent.

The conventional approach to treatment of nail fungus is to debride the nail manually to remove as much of the keratin caused by the thickening of the fungus, in order that penetrations of antifungal medicines can result. Additionally application of antikeratolytics, such as salicylic acid or urea, are also used to remove keratin debris. The reason for this is that keratin is layered as a protective shield against penetration of substances. It is found in the skin as well. Some conventional products use various substances to enhance penetration with limited success such as alcohol, polyethylene glycol, triglycerides, fatty acids, liposomes, nanospheres, or lecithin. These all have limited ability to penetrate the skin and are essentially of no use on a thick layer of keratin in toenails. Because the cell membranes are made of phospholipids, fat soluble substances can pass between cells called desmosome connections, through cell membranes and through keratin. U.S. Pat. No. 6,344,190 discloses a composition for treatment of dermatophytes that contains several essential oil components and a carrier system. However, the disclosed compositions do not teach a carrier system or combination of specific essential oils such as required in the present invention composition. Namely, the only carrier systems specifically named in the '190 patent appear to be an alcohol ester, such as isoamyl alcohol (an evaporative carrier) or a commercially available product designated VICKS VAPO-RUB (a thick greasy carrier system containing a mixture of unidentified ingredients).

The present invention composition and method use a carrier that penetrates the keratin by being a fat soluble substance, such as hydrocarbons. One preferred carrier is mineral oil, which is a fat solvent, when combined with turpentine and, optionally, with camphor (a distillation derivative obtained from pine or from the cinnamomum camphor tree, a monoterpenoid), and/or one or more other terpenoid substances. The liquid carrier of the present invention comprises the combination of a mineral oil and pine(turpentine). This preferred combination of carrier components helps to pull the antifungal essential oils of the present invention antifungal composition through the thick layers of keratin found in the nail. The present composition does not require debridement of the nails or keratolytics in order to be effective. The present composition has been found effective in treating nail fungus just by application directly to the nail surface on a regular basis. However, while not requiring the above, the present composition can be used in combination with debridement or added keratolytics, if desired.

Additionally, the components contained in the present invention composition are considered GRAS (generally recognized as safe) under U.S. FDA regulations, and therefore can be sold as an over-the-counter composition.

To reach the desired area the carrier must be fat soluble (i.e., will dissolve in fat, remain soluble and forms an essentially homogeneous solution with fat) and the antifungal agents must also be fat soluble to penetrate these intercellular fat soluble connections, as well as the keratin. To be effective, the formula must have the ability to penetrate the toenail (i.e. move across phospholipid cell membrane, fatty bilayer of keratin (through keratin), and desmosomes. Most conventional antifungal compositions are not effective on toenails (absent debridement or keratolytics) because they are not able to get the antifungal composition thru the nail plate and skin under the nail called the nail bed.

The present composition has been found to be effective on substantially all types of nail fungus disorders, whether of distal type, lateral type, superficial type, or proximal type involving the whole nail. Studies using sequential photography have shown its effectiveness as 40% cure rate and 25% almost cure rate/improvement. Importantly, the present composition does not require debridement of the nail to be effective, because the vehicle for penetration of the nail plate works regardless of the thickness of the nail. The composition is also broad spectrum, which is necessary because these organism are polymorphic and can change their resistance. The combination of multiple effective antifungal essential oils in the present composition allow for this. While the preferred use for the present composition is treatment of onychomycotic toenails, the composition can be used to treat skin fungus infections as well. Upon treatment of nail fungus with the present composition, it has been noted that the nails appear to grow faster as treatment progresses. This may be due to increased nail growth as a result of decreasing the fungal involvement, or by stimulation of the nail matrix by the present composition.

The present composition can be in any form suitable for topical application, particularly to the nail surface. The composition can preferably take a form including, but not limited to, liquid solutions, liquid suspensions, liquid dispersions, gels, jellies, crèmes, and ointments. Most preferably for application to the nail, the composition is in the form of a liquid, either in solution, suspension or dispersion form. For use on skin, either liquid or gel/jelly forms are preferred. In use on skin, the composition preferably contains petrolatum as an additional carrier. The petrolatum may be as is, or may be treated with ultraviolet light (preferably using a cold UV lamp), which has been reported to provide additional healing properties through a property called "radiolatum".

Although not required in the present composition, the composition can optionally contain one or more keratolytic agents, such as salicylic acid or urea, as well as other conventional additives and/or auxiliaries used in topical compositions. Such conventional additives or auxiliaries include, but are not limited to, fillers, colorants or dyes, skin conditioners, MSM (methylsulfoxymethane), etc.

Nail fungi are parasites that live and grow in the nail and underlying skin called nail bed. The fungus lives off the keratin of the nail and causes the nail to produce more keratin. The fungus produces spores and tentacles called hyphae that grow out. The fungus also produces keratinases to eat away at the keratin as well. The keratin is a protein, and like the outside layer of the skin, tends to prevent things from penetrating. When the fungus does invade the toenail, it eats away and rots it, much like a rotting piece of wood. While plants and trees have natural antibiotic oils in their leaves and bark, to keep away these invaders, human tissue does not have the same advantage. Based on this principal, the present composition uses a mixture of antifungal essential oils. However, the oils alone still have a difficult time penetrating the thick keratin nail plate. Prior to the present invention, so far as is known by the present inventor, no one has found a way to do this effectively as a topical agent. With the present invention composition, the antifungal essential oils are carried or delivered through this tough, up to now impenetrable, barrier. The present composition provides a mixture of antifungal essential oils that is a broad spectrum antifungal combination so as to cover all the mutant resistances that develop, prevents keep the fungus from growing, and is not harmful to the nail or nail matrix.

The present invention carrier or delivery system comprises a mineral oil (lipid solvent), and turpentine, and optionally camphor and/or one or more additional terpenoids containing pinene. (In addition, several of the anti-fungal essential oils can act both in an antifungal role as well as a carrier role, such as camphor (which can be distilled from pine)., The antifungal essential oils are preferably plant extracts and are fat soluble. The composition comprises a mixture of antifungal essential oils comprising camphor, eucalyptus globulus, peppermint, cedarwood oil (cedar atlas from *cedrus atlantica*), and manuka oil (from *lepospermum scoparium*). In addition to these, the mixture of antifungal essential optionally can further comprise amounts of sage, juniper, clove, lavender, cinnamon bark and leaf oil, grapeseed, jojoba oil, anise, rosewood, *eucalyptus citroidora*, tea tree (from *malaleuca alternafolia*), and nutmeg. Importantly, the mixture of antifungal essential oils is preferably substantially free of the presence of thymol. Within the context of the present invention, the term "substantially free of thymol" is used to indicate that the essential oils used do not have detectable amounts of thymol, as determined by gas chromatographic analysis of the essential oil itself. In one embodiment of the present invention, the composition further comprises grapeseed extract and anise, which together increase effectiveness of the composition against yeasts known as polygyols, potentially up to a 30-40 fold increase in effectiveness.

The amount of each antifungal essential oil used is preferably in the range of from 0.1% to 40%, based on total composition amount. More preferably, the antifungal essential oils are present in an amount of from 0.1% to 10%, most preferably from 1% to 7%, based on total composition amount. These amounts do not have to be the same for each antifungal essential oil, and the amount of each individual essential oil present in the composition is independent of the identity or amount of other components used. The carrier components are preferably each, independently, present in amounts of from 0.1-40% by weight, based on total composition amount. More preferably, the mineral oil is present in an amount of from 5-30% by weight. The turpentine can also be in similar amounts as mineral oil, with camphor (when present) being present preferably in smaller amounts, comparable to the amount of individual antifungal essential oils. Camphor can act both as part of the carrier system and as one of the antifungal essential oils of the antifungal composition of the present invention. The carrier system itself can be used for delivery of any desired fat soluble active agent(s), particularly for treatment of disorders related to keratinous tissues.

The method for using the present composition comprises application of the composition directly to the nail surface. Preferably, the applications are performed from 1 to 4 applications per day, and are continued until the infection is eliminated, preferably for a period of 3 to 12 months. Afterward, the composition can be used on a regular basis (approximately every 2-3 days) to prevent reoccurrence of the infection and encourage nail health. More preferably, the composition is applied from 1 to 2 times per day directly to the nail surface, most preferably immediately after bathing. The application is performed using any type of applicator, including but not limited to, fingers, brushes, swabs, etc. The application should preferably be sufficient to form a thin film of the composition on most or all of the nail surface. While the application can also include the skin area surrounding the nail, this can cause temporary skin irritation in some patients.

EXAMPLES

Based on application to a patient group of over 150 patients, application of the antifungal composition of the present invention gave a conservative estimate of 40-60% cure, with a rate of cure/improvement in the 66-85% range. Patients were instructed to apply the composition twice daily after bathing, then were individually observed on a monthly basis. Pictures can be taken to document recovery. If complete nail involvement was present, the total nail may take up to 9-12 months to grow out. Less involvement takes a shorter period of time, typically ⅓-½ of the time.

A most preferred example of the present antifungal composition contains the following:

| Essential Oils | |
|---|---|
| *Eucalyptus globulus* | 5% |
| Peppermint | 5% |
| Cedarwood | 5% |
| Manuka | 5% |
| Sage | 5% |
| Juniper | 5% |
| Clove | 5% |
| Lavender | 5% |
| Cinnamon bark and leaf oil | 5% |
| Jojoba oil | 5% |
| Grapeseed | 5% |
| Anise | 5% |
| Tea Tree | 5% |
| Rosewood | 5% |
| *Eucalyptus citroidia* | 2.5% |
| Nutmeg | 5% |
| Carrier System | |
| Mineral oil | 12.5% |
| Camphor | 5% |
| Turpentine | 5% |

The invention claimed is:

1. A method for the treatment of fungal infection, comprising:
    topically applying to an area of skin or nail in need thereof, an effective amount of a composition comprising:
    an effective anti-fungal amount of a mixture of fat-soluble essential oils and a carrier system,
    wherein the mixture of fat-soluble essential oils comprises an amount of from 0.1 to 10% by weight, based on total composition amount, of each of Eucalyptus globulus oil, peppermint oil, cedarwood oil, and manuka oil; and
    wherein the carrier system comprises a mineral oil and turpentine; wherein each of the mineral oil and turpentine are present in an amount of from 0.1-40% by weight.

2. The method of claim 1, wherein said topically applying is to an area of nail in need thereof.

3. The method of claim 2, wherein said topically applying is performed so as to form a thin film of said composition on an entire surface of the nail.

4. The method of claim 1, wherein the carrier system further comprises one or more additional terpenoid components containing pinene.

5. The method of claim 1, wherein said carrier system further comprises camphor.

6. The method of claim 1, wherein said mixture of fat-soluble antifungal essential oils further comprises one or more of sage oil, juniper oil, clove oil, lavender oil, Cinnamomum bark and leaf oil, jojoba oil, grapeseed oil, anise oil, tea tree oil, rosewood oil, *Eucalyptus citroidora* oil, and nutmeg oil.

7. The method of claim 1, wherein said mixture of antifungal essential oils is substantially free of thymol.

8. The method of claim 1, wherein the composition is in a form selected from the group consisting of liquid solutions, liquid suspensions, liquid dispersions, gels, jellies, crèmes, and ointments.

9. The method of claim 8, wherein said composition is in a form selected from the group consisting of liquid solutions, liquid suspensions and liquid dispersions.

10. The method of claim 9, wherein said composition is a liquid solution.

11. A method for the delivery of an active agent through nail tissue containing keratin, comprising:
   topically applying to an area of nail, a liquid composition comprising a carrier system comprising a mineral oil and turpentine; and
   active agents;
   wherein the active agents comprise a mixture of fat-soluble antifungal essential oils in an amount of from 0.1 to 10% by weight, based on total composition amount, of each of *Eucalyptus globulus* oil, peppermint oil, cedarwood oil, and manuka oil; and
   wherein each of the mineral oil and turpentine are present in an amount of from 0.1-40% by weight.

12. The method of claim 11, wherein said topically applying is performed so as to form a thin film of said liquid composition on an entire surface of the nail.

13. The method of claim 11, wherein the carrier system further comprises one or more additional terpenoid components containing pinene.

14. The method of claim 11, wherein said carrier system further comprises camphor.

15. The method of claim 11, wherein said mixture of fat-soluble antifungal essential oils further comprises one or more of sage oil, juniper oil, clove oil, lavender oil, Cinnamomum bark and leaf oil, jojoba oil, grapeseed oil, anise oil, tea tree oil, rosewood oil, *Eucalyptus citroidora* oil, and nutmeg oil.

16. The method of claim 11, wherein said composition is in a form selected from the group consisting of liquid solutions, liquid suspensions and liquid dispersions.

17. The method of claim 11, wherein said composition is a liquid solution.

* * * * *